United States Patent
Migliazza et al.

(10) Patent No.: US 9,687,346 B2
(45) Date of Patent: Jun. 27, 2017

(54) MULTI-STRANDED HEAT SET ANNULOPLASTY RINGS

(71) Applicant: Edwards Lifesciences Corporation, Irvine, CA (US)

(72) Inventors: John F. Migliazza, Belmont Shores, CA (US); Ruggero De Paulis, Rome (IT)

(73) Assignee: Edwards Lifesciences Corporation, Irvine, CA (US)

(*) Notice: Subject to any disclaimer, the term of this patent is extended or adjusted under 35 U.S.C. 154(b) by 298 days.

(21) Appl. No.: 14/189,842

(22) Filed: Feb. 25, 2014

(65) Prior Publication Data

US 2014/0277420 A1    Sep. 18, 2014

Related U.S. Application Data

(60) Provisional application No. 61/784,010, filed on Mar. 14, 2013.

(51) Int. Cl.
*A61F 2/24* (2006.01)
*C22F 1/10* (2006.01)

(52) U.S. Cl.
CPC .......... *A61F 2/2445* (2013.01); *A61F 2/2448* (2013.01); *C22F 1/10* (2013.01);
(Continued)

(58) Field of Classification Search
CPC .......... A61F 2/2445; A61F 2310/00005; A61F 2250/0042; A61F 2/2415; Y10T 29/49986;
(Continued)

(56) References Cited

U.S. PATENT DOCUMENTS 3,656,185 A    4/1972  Carpentier
4,055,861 A    11/1977 Carpentier et al.
(Continued)

FOREIGN PATENT DOCUMENTS

EP    0338994 A1    10/1989
EP    0860151 A1    8/1998
(Continued)

OTHER PUBLICATIONS

Adams, David, et al., "Large Annuloplasty Rings Facilitate Mitral Valve Repair in Barlow's Disease," Society of Thoracic Surgeons 42nd Annual Meeting, Jan. 30-Feb. 1, 2006.
(Continued)

*Primary Examiner* — John C Hong
(74) *Attorney, Agent, or Firm* — Guy Cumberbatch; Thomas C. Richardson

(57) ABSTRACT

An annuloplasty repair segment for heart valve annulus repair. In one embodiment a multi-stranded cable replaces solid core wire for both the tricuspid and mitral valves. Cable allows for greater deployment flexibility for minimally-invasive surgical (MIS) implant, while still maintaining the required strength and similar tensile properties of solid-core wire. Stranded cable provides a MIS annuloplasty ring with sufficient flexibility in the x-y plane to allow a surgeon to squeeze the ring into a small incision, such as being able to pass through an 18 Fr or smaller catheter, while maintaining structural rigidity under forces exerted on the implanted ring by the cardiac cycle. The particular shape of the annuloplasty ring is fixed using a heat setting process.

13 Claims, 5 Drawing Sheets

(52) U.S. Cl.
CPC .......... *A61F 2/2415* (2013.01); *A61F 2/2466* (2013.01); *A61F 2210/0019* (2013.01); *A61F 2230/0095* (2013.01); *A61F 2240/001* (2013.01); *A61F 2250/0042* (2013.01); *A61F 2310/00005* (2013.01); *Y10T 29/4989* (2015.01); *Y10T 29/49826* (2015.01); *Y10T 29/49844* (2015.01); *Y10T 29/49865* (2015.01); *Y10T 29/49908* (2015.01); *Y10T 29/49948* (2015.01); *Y10T 29/49968* (2015.01); *Y10T 29/49986* (2015.01); *Y10T 29/49998* (2015.01); *Y10T 29/5353* (2015.01)

(58) Field of Classification Search
CPC ......... Y10T 29/49948; Y10T 29/49968; Y10T 29/49908; Y10T 29/49998; Y10T 29/49865; Y10T 29/49844; Y10T 29/4989; Y10T 29/5353; Y10T 29/49826
See application file for complete search history.

(56) References Cited

U.S. PATENT DOCUMENTS

| | | |
|---|---|---|
| 4,164,046 A | 8/1979 | Cooley |
| 4,217,665 A | 8/1980 | Bex et al. |
| 4,275,469 A | 6/1981 | Gabbay |
| 4,602,911 A | 7/1986 | Ahmadi et al. |
| 4,790,844 A | 12/1988 | Ovil |
| 4,917,097 A | 4/1990 | Proudian et al. |
| 4,917,698 A | 4/1990 | Carpentier et al. |
| 4,993,428 A | 2/1991 | Arms |
| 5,010,892 A | 4/1991 | Colvin et al. |
| 5,041,130 A | 8/1991 | Cosgrove et al. |
| 5,061,275 A * | 10/1991 | Wallsten .............. A61F 2/90 623/1.22 |
| 5,061,277 A | 10/1991 | Carpentier et al. |
| 5,064,431 A | 11/1991 | Gilbertson et al. |
| 5,104,407 A | 4/1992 | Lam et al. |
| 5,201,880 A | 4/1993 | Wright et al. |
| 5,258,021 A | 11/1993 | Duran |
| 5,306,296 A | 4/1994 | Wright et al. |
| 5,316,016 A | 5/1994 | Adams et al. |
| 5,344,442 A | 9/1994 | Deac |
| 5,396,887 A | 3/1995 | Imran |
| 5,397,348 A | 3/1995 | Campbell et al. |
| 5,450,860 A | 9/1995 | O'Connor |
| 5,480,424 A | 1/1996 | Cox |
| 5,496,336 A | 3/1996 | Cosgrove et al. |
| 5,533,515 A | 7/1996 | Coller et al. |
| 5,573,007 A | 11/1996 | Bobo, Sr. |
| 5,593,435 A | 1/1997 | Carpentier et al. |
| 5,607,471 A | 3/1997 | Seguin et al. |
| 5,662,704 A | 9/1997 | Gross |
| 5,674,279 A | 10/1997 | Wright et al. |
| 5,716,397 A | 2/1998 | Myers |
| 5,728,064 A | 3/1998 | Burns et al. |
| 5,733,331 A | 3/1998 | Peredo |
| 5,752,522 A | 5/1998 | Murphy |
| 5,776,189 A | 7/1998 | Khalid |
| 5,814,098 A | 9/1998 | Hinnenkamp et al. |
| 5,824,066 A | 10/1998 | Gross |
| 5,824,069 A | 10/1998 | Lemole |
| 5,848,969 A | 12/1998 | Panescu et al. |
| 5,855,563 A | 1/1999 | Kaplan et al. |
| 5,865,801 A | 2/1999 | Houser |
| 5,888,240 A | 3/1999 | Carpentier et al. |
| 5,902,308 A | 5/1999 | Murphy |
| 5,919,147 A | 7/1999 | Jain |
| 5,921,934 A | 7/1999 | Teo |
| 5,921,935 A | 7/1999 | Hickey |
| 5,924,984 A | 7/1999 | Rao |
| 5,931,868 A | 8/1999 | Gross |
| 5,972,030 A | 10/1999 | Garrison et al. |
| 6,010,531 A | 1/2000 | Donlon et al. |
| 6,019,739 A | 2/2000 | Rhee et al. |
| 6,024,918 A | 2/2000 | Hendriks et al. |
| 6,042,554 A | 3/2000 | Rosenman et al. |
| 6,066,160 A | 5/2000 | Colvin et al. |
| 6,081,737 A | 6/2000 | Shah |
| 6,083,179 A | 7/2000 | Oredsson |
| 6,099,475 A | 8/2000 | Seward et al. |
| 6,102,945 A | 8/2000 | Campbell |
| 6,110,200 A | 8/2000 | Hinnenkamp |
| 6,117,091 A | 9/2000 | Young et al. |
| 6,143,024 A | 11/2000 | Campbell et al. |
| 6,159,240 A | 12/2000 | Sparer et al. |
| 6,183,512 B1 | 2/2001 | Howanec, Jr. et al. |
| 6,187,040 B1 | 2/2001 | Wright |
| 6,217,610 B1 | 4/2001 | Carpentier et al. |
| 6,231,602 B1 | 5/2001 | Carpentier et al. |
| 6,250,308 B1 | 6/2001 | Cox |
| 6,258,122 B1 | 7/2001 | Tweden et al. |
| 6,312,464 B1 | 11/2001 | Navia |
| 6,332,893 B1 | 12/2001 | Mortier et al. |
| 6,348,068 B1 | 2/2002 | Campbell et al. |
| 6,368,348 B1 | 4/2002 | Gabbay |
| 6,391,054 B2 | 5/2002 | Carpentier et al. |
| 6,406,420 B1 | 6/2002 | McCarthy et al. |
| 6,406,493 B1 | 6/2002 | Tu et al. |
| 6,409,759 B1 | 6/2002 | Peredo |
| 6,419,696 B1 | 7/2002 | Ortiz et al. |
| 6,524,338 B1 | 2/2003 | Gundry |
| 6,602,288 B1 | 8/2003 | Cosgrove et al. |
| 6,602,289 B1 | 8/2003 | Colvin et al. |
| 6,619,291 B2 | 9/2003 | Hlavka et al. |
| 6,709,456 B2 | 3/2004 | Langberg et al. |
| 6,718,985 B2 | 4/2004 | Hlavka et al. |
| 6,719,786 B2 | 4/2004 | Ryan et al. |
| 6,723,038 B1 | 4/2004 | Schroeder et al. |
| 6,726,715 B2 | 4/2004 | Sutherland |
| 6,726,717 B2 | 4/2004 | Alfieri et al. |
| 6,749,630 B2 | 6/2004 | McCarthy et al. |
| 6,764,510 B2 | 7/2004 | Vidlund et al. |
| 6,790,231 B2 | 9/2004 | Liddicoat et al. |
| 6,797,002 B2 | 9/2004 | Spence et al. |
| 6,800,090 B2 | 10/2004 | Alferness et al. |
| 6,802,860 B2 | 10/2004 | Cosgrove et al. |
| 6,805,710 B2 | 10/2004 | Bolling et al. |
| 6,805,711 B2 | 10/2004 | Quijano et al. |
| 6,830,586 B2 | 12/2004 | Quijano et al. |
| 6,858,039 B2 | 2/2005 | McCarthy |
| 6,908,482 B2 | 6/2005 | McCarthy et al. |
| 6,918,917 B1 | 7/2005 | Nguyen et al. |
| 6,921,407 B2 | 7/2005 | Nguyen et al. |
| 6,942,694 B2 | 9/2005 | Liddicoat et al. |
| 6,945,996 B2 | 9/2005 | Sedransk |
| 6,955,689 B2 | 10/2005 | Ryan et al. |
| 6,962,605 B2 | 11/2005 | Cosgrove et al. |
| 6,966,924 B2 | 11/2005 | Holmberg |
| 6,977,950 B1 | 12/2005 | Krishnamoorthy |
| 6,986,775 B2 | 1/2006 | Morales et al. |
| 7,037,334 B1 | 5/2006 | Hlavka et al. |
| 7,066,954 B2 | 6/2006 | Ryan et al. |
| 7,101,395 B2 | 9/2006 | Tremulis et al. |
| 7,112,219 B2 | 9/2006 | Vidlund et al. |
| 7,118,595 B2 | 10/2006 | Ryan et al. |
| 7,125,421 B2 | 10/2006 | Tremulis et al. |
| 7,166,126 B2 | 1/2007 | Spence et al. |
| 7,166,127 B2 | 1/2007 | Spence et al. |
| 7,247,134 B2 | 7/2007 | Vidlund et al. |
| 7,294,148 B2 | 11/2007 | McCarthy |
| 7,314,485 B2 | 1/2008 | Mathis |
| 7,329,280 B2 | 2/2008 | Bolling et al. |
| 7,361,190 B2 | 4/2008 | Shaoulian et al. |
| 7,452,376 B2 | 11/2008 | Lim et al. |
| 7,527,647 B2 | 5/2009 | Spence |
| 7,608,103 B2 | 10/2009 | McCarthy |
| 7,655,040 B2 | 2/2010 | Douk et al. |
| 7,699,892 B2 | 4/2010 | Rafiee et al. |
| 7,959,673 B2 | 6/2011 | Carpentier et al. |
| 7,993,395 B2 | 8/2011 | Vanermen et al. |
| 8,034,103 B2 | 10/2011 | Burriesci et al. |
| 8,123,802 B2 | 2/2012 | Kron et al. |
| 8,460,173 B2 | 6/2013 | Schweich, Jr. et al. |

(56) References Cited

U.S. PATENT DOCUMENTS

| | | |
|---|---|---|
| 8,535,374 B2 | 9/2013 | Redmond et al. |
| 8,591,576 B2 | 11/2013 | Hasenkam et al. |
| 8,734,507 B2 | 5/2014 | Keranen |
| 8,764,821 B2 | 7/2014 | Carpentier et al. |
| 2001/0034551 A1 | 10/2001 | Cox |
| 2002/0129820 A1 | 9/2002 | Ryan et al. |
| 2002/0133180 A1 | 9/2002 | Ryan et al. |
| 2002/0169504 A1 | 11/2002 | Alferness et al. |
| 2002/0173844 A1 | 11/2002 | Alfieri et al. |
| 2003/0033009 A1 | 2/2003 | Gabbay |
| 2003/0040793 A1 | 2/2003 | Marquez |
| 2003/0045929 A1 | 3/2003 | McCarthy et al. |
| 2003/0078653 A1 | 4/2003 | Vesely et al. |
| 2003/0083742 A1 | 5/2003 | Spence et al. |
| 2003/0093148 A1 | 5/2003 | Bolling et al. |
| 2003/0105519 A1 | 6/2003 | Fasol et al. |
| 2004/0006384 A1 | 1/2004 | McCarthy |
| 2004/0088047 A1 | 5/2004 | Spence et al. |
| 2004/0122513 A1 | 6/2004 | Navia et al. |
| 2004/0186566 A1 | 9/2004 | Hindrichs et al. |
| 2004/0249452 A1 | 12/2004 | Adams et al. |
| 2004/0249453 A1 | 12/2004 | Cartledge et al. |
| 2005/0004666 A1 | 1/2005 | Alfieri et al. |
| 2005/0043791 A1 | 2/2005 | McCarthy et al. |
| 2005/0070999 A1 | 3/2005 | Spence |
| 2005/0075727 A1 | 4/2005 | Wheatley |
| 2005/0131533 A1 | 6/2005 | Alfieri et al. |
| 2005/0182487 A1 | 8/2005 | McCarthy et al. |
| 2005/0192666 A1 | 9/2005 | McCarthy |
| 2005/0197696 A1 | 9/2005 | Gomez Duran |
| 2005/0246014 A1 | 11/2005 | McCarthy |
| 2005/0256567 A1 | 11/2005 | Lim et al. |
| 2005/0256568 A1 | 11/2005 | Lim et al. |
| 2005/0256569 A1 | 11/2005 | Lim et al. |
| 2005/0267572 A1 | 12/2005 | Schoon et al. |
| 2005/0278022 A1 | 12/2005 | Lim |
| 2005/0288776 A1 | 12/2005 | Shaoulian et al. |
| 2005/0288777 A1 | 12/2005 | Rhee et al. |
| 2005/0288778 A1 | 12/2005 | Shaoulian et al. |
| 2005/0288780 A1 | 12/2005 | Rhee et al. |
| 2005/0288782 A1 | 12/2005 | Moaddeb et al. |
| 2005/0288783 A1 | 12/2005 | Shaoulian et al. |
| 2006/0015178 A1 | 1/2006 | Moaddeb et al. |
| 2006/0015179 A1 | 1/2006 | Bulman-Fleming et al. |
| 2006/0020336 A1 | 1/2006 | Liddicoat |
| 2006/0025856 A1 | 2/2006 | Ryan et al. |
| 2006/0025858 A1 | 2/2006 | Alameddine |
| 2006/0030885 A1 | 2/2006 | Hyde |
| 2006/0129236 A1 | 6/2006 | McCarthy |
| 2006/0149368 A1 | 7/2006 | Spence |
| 2006/0184241 A1 | 8/2006 | Marquez |
| 2006/0195183 A1 | 8/2006 | Navia et al. |
| 2006/0206203 A1 | 9/2006 | Yang et al. |
| 2006/0247491 A1 | 11/2006 | Vidlund et al. |
| 2006/0259135 A1 | 11/2006 | Navia et al. |
| 2007/0027533 A1 | 2/2007 | Douk |
| 2007/0038294 A1 | 2/2007 | Navia |
| 2007/0049952 A1 | 3/2007 | Weiss |
| 2007/0050020 A1 | 3/2007 | Spence |
| 2007/0066863 A1 | 3/2007 | Rafiee et al. |
| 2007/0100439 A1 | 5/2007 | Cangialosi et al. |
| 2007/0118151 A1 | 5/2007 | Davidson |
| 2007/0123979 A1 | 5/2007 | Perier et al. |
| 2007/0162111 A1 | 7/2007 | Fukamachi et al. |
| 2007/0162112 A1 | 7/2007 | Burriesci et al. |
| 2007/0173930 A1 | 7/2007 | Sogard et al. |
| 2007/0213582 A1 | 9/2007 | Zollinger et al. |
| 2007/0255396 A1 | 11/2007 | Douk et al. |
| 2008/0086203 A1* | 4/2008 | Roberts ............. A61F 2/2448 623/2.36 |
| 2008/0269878 A1 | 10/2008 | Iobbi |
| 2009/0043381 A1 | 2/2009 | Macoviak et al. |
| 2009/0177276 A1 | 7/2009 | Carpentier et al. |
| 2009/0177278 A1 | 7/2009 | Spence |
| 2009/0192602 A1 | 7/2009 | Kuehn |
| 2009/0192603 A1 | 7/2009 | Ryan |
| 2009/0192604 A1 | 7/2009 | Gloss |
| 2009/0192605 A1 | 7/2009 | Gloss et al. |
| 2009/0192606 A1 | 7/2009 | Gloss et al. |
| 2009/0287303 A1 | 11/2009 | Carpentier |
| 2010/0161025 A1* | 6/2010 | Kuppurathanam ....... A61F 2/07 623/1.13 |
| 2010/0161047 A1 | 6/2010 | Cabiri |
| 2010/0168845 A1 | 7/2010 | Wright |
| 2010/0211166 A1 | 8/2010 | Miller et al. |
| 2011/0004298 A1 | 1/2011 | Lee et al. |
| 2011/0112624 A1 | 5/2011 | Molaei |
| 2011/0166649 A1 | 7/2011 | Gross et al. |
| 2012/0053687 A1* | 3/2012 | Migliazza ............ A61F 2/2448 623/2.37 |
| 2012/0078359 A1 | 3/2012 | Li et al. |
| 2012/0310330 A1 | 12/2012 | Buchbinder et al. |
| 2013/0325095 A1* | 12/2013 | Ollivier ................ A61N 1/0587 607/129 |

FOREIGN PATENT DOCUMENTS

| | | |
|---|---|---|
| EP | 1034753 A1 | 9/2000 |
| GB | 2189150 A | 10/1987 |
| WO | 9742871 A1 | 11/1997 |
| WO | 98/14138 A1 | 4/1998 |
| WO | 99/49816 A1 | 10/1999 |
| WO | 01/08608 A1 | 2/2001 |
| WO | 2005/004753 A1 | 1/2005 |
| WO | 2005/034813 A2 | 4/2005 |
| WO | 2008/063537 A2 | 5/2008 |

OTHER PUBLICATIONS

Alonso-Lei, M.D., et al., Adjustable Annuloplasty for Tricuspid Insufficiency, The annals of Thoracic Surgery, vol. 46, No. 3, pp. 368-369, Sep. 1988.

Bolling, et al., Surgical Alternatives for Heart Failure, The Journal of Heart and Lung Transplantation, vol. 20, No. 7, pp. 729-733, 2001.

Bolling, Mitral Valve Reconstruction in the Patient With Heart Failure, Heart Failure Reviews, 6, pp. 177-185, 2001.

Caleya, et al., "Fracture of Carpentier's Ring in a Patient with Tricuspid Annuloplasty". Thoracic Cardiovascular Surgeon. vol. 31. pp. 175-176. 1983.

Carpentier, et al. "The 'Physio-Ring': An Advanced Concept in Mitral Valve Annuloplasty," Society of Thoracic Surgeons 31st Annual meeting, Jan. 30-Feb. 2, 1995.

Carpentier, et al., "Reconstructive Valve Surgery" Chapters 17-19, ISBN No. 978-0-7216-9168-8, Sanders Elsevier Publishing, Maryland Heights, Missouri, 2010.

Carpentier-Edwards Classic Annuloplasty Ring With Duraflo Treatment Models 4425 and 4525 for Mitral and Tricuspid Valvuloplsty, Baxter Healthcare Corporation, 1998.

Carpentier-Edwards Pyshio Annuloplasty Ring, Edwards Lifesciences Corporation, 2003.

Cochran, et al., "Effect of Papillary muscle Position on Mitral Valve Function: Relationship to Homografts," The Society of Thoracic Surgeons, pp. 5155-5161, 1998.

Cosgrove, et al., "Initial Experience with the Cosgrove-Edwards Annuloplasty System," The Annals of Thoracic Surgery. vol. 60. pp. 499-504, 1995.

Cosgrove-Edwards, "Annuloplasty System," Edwards Lifesciences Corporation, 2000.

D.C. Miller, IMR Redux—To Repair or Replace?, Journal of Thoracic & Cardiovascular Surgery, pp. 1-8, 2001.

Flachskampf, Frank A., et al. "Analysis of Shape and Motion of the Mitral Annulus in Subjects With and Without Cardiomyopathy by Echocardiographic 3-Dimensional Reconstruction," American Society of Echocardiography 0894-7317/2000.

Galinanes, et al., "Fracture of the Carpentier-Edwards Ring in Tricuspid Position: A Report of Three Cases," The Annals of Thoracic Surgery, vol. 42, pp. 74-76, 1986.

(56) References Cited

OTHER PUBLICATIONS

Gatti, et al., Preliminary Experience in Mitral Valve Repair Using the Cosgrove-Edwards Annuloplasty Ring, Interactive Cardiovascular and Thoracic Surgery, vol. 2(3), pp. 256-261, 2003.
Melo, et al., Atrioventricular Valve Repair Using Externally Adjustable Flexible Rings: The Journal of Thoracic cardiovascular Surgery, vol. 110, No. 5, 1995.
MGH Study Shows Mitral Valve Prolapse Not a Stroke Risk Factor, Massachusetts General Hospital, pp. 1-3, Jun. 1999.
Navia, Jose Luis., "Minimally Invasive Mitral Valve Surgery," Department of Thoracic and Cardiovascular Surgery, The Cleveland Clinic Foundation, 2001.
Salgo, et al., Effect of Annular Shape on Leaflet Curvature in Reducing Mitral Leaflet, American Heart Association, Circulation 2002; pp. 106-711.
Seguin, et al., Advance in Mitral Valve Repair Using a Device Flexible in Three Dimensions, The St. Jude Medical-Seguin Annuloplasty Ring, ASAIO Journal, vol. 42, No. 6, pp. 368-371, 1996.
Smolens, et al., Mitral Valve Repair in Heart Failure, The European Journal of Heart Failure 2, pp. 365-371, 2000.
Watanabe, Nozomi, et al. "Mitral Annulus Flattens in Ischemic Mitral Regurgitation: Geometric Differences Between Inferior and Anterior Myocardial Infarction: A Real-Time 3-Dimensional Echocardiographic Study," American Heart Association © 2005; ISSN: 1524-4539.
Mohammad, H. Elahinia et al., "Manufacturing and processing of NiTi implants: A review", Progress in Materials Science., vol. 57, No. 5, Nov. 17, 2011, pp. 911-946.
Yeung Kwk et al, "Optimization of thermal treatment parameters to alter austenitic phase transition temperature of NiTi alloy medical implant", Materials Science and Engineering A: Structural Materials : Properties, Microstructures and Processing, Elsevier BV, NL, vol. 383, No. 2, Oct. 15, 2004.

\* cited by examiner

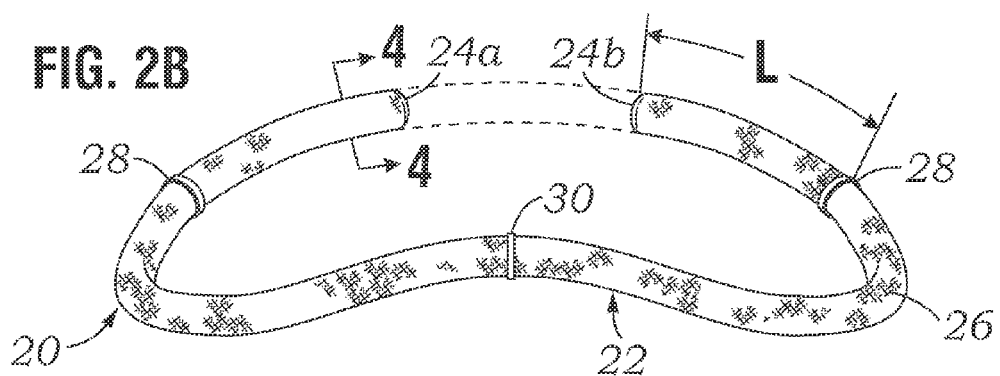
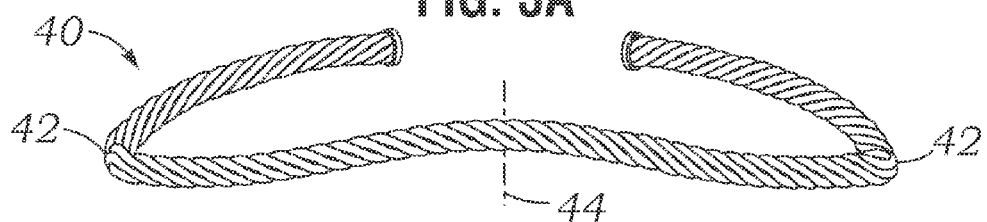
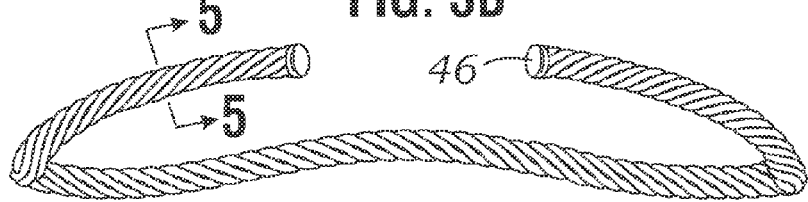
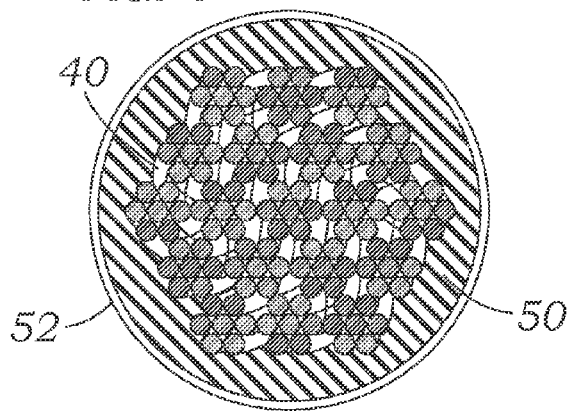
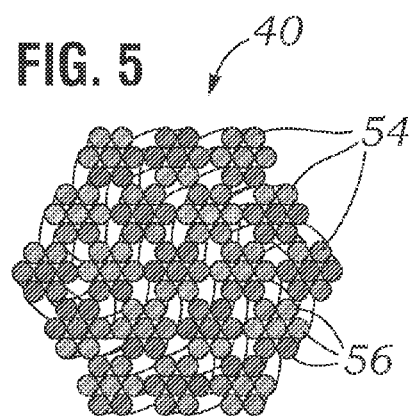

FIG. 11A
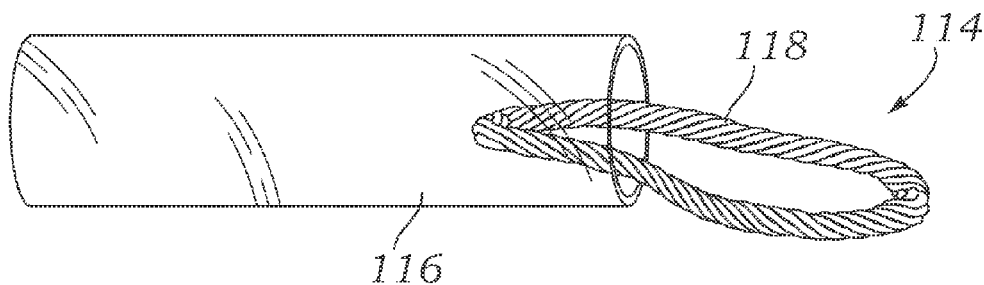
FIG. 12A
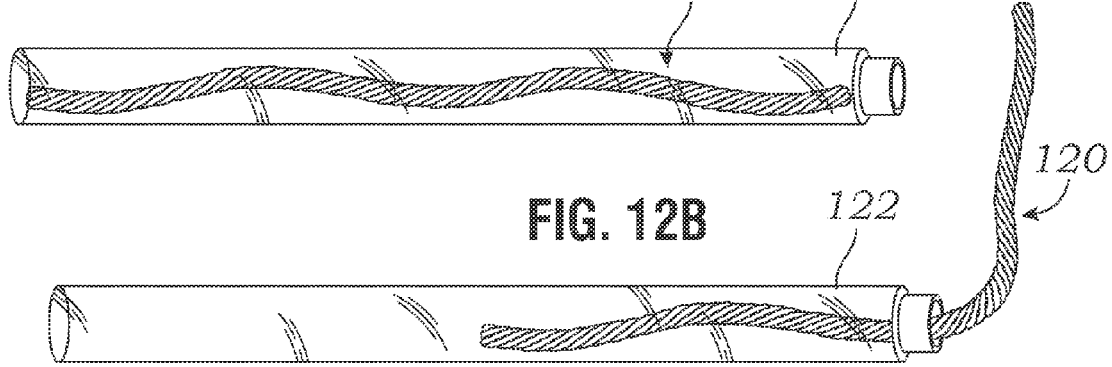
FIG. 12B

MULTI-STRANDED HEAT SET ANNULOPLASTY RINGS

RELATED APPLICATIONS

The present application claims priority under 35 U.S.C. §119(e) to Provisional Application No. 61/784,010, filed on Mar. 14, 2013.

FIELD OF THE INVENTION

The present invention relates generally to cardiac implants and particularly to flexible annuloplasty rings having stranded core members heat set into desired shapes.

BACKGROUND OF THE INVENTION

In vertebrate animals, the heart is a hollow muscular organ having four pumping chambers: the left and right atria and the left and right ventricles, each provided with its own one-way valve. The natural heart valves are identified as the aortic, mitral (or bicuspid), tricuspid and pulmonary, and are each mounted in an annulus comprising dense fibrous rings attached either directly or indirectly to the atrial and ventricular muscle fibers. Each annulus defines a flow orifice.

Prosthetic annuloplasty rings are used to repair or reconstruct damaged or diseased heart valve annuluses. An annuloplasty ring is designed to support the functional changes that occur during the cardiac cycle: maintaining leaflet coaptation and valve integrity to prevent reverse flow while permitting good hemodynamics during forward flow. The annuloplasty techniques may be used in conjunction with other repair techniques. The rings either partially or completely encircle the valve, and may be rigid, flexible, or selectively flexible.

Although mitral valve repair and replacement can successfully treat many patients with mitral valve insufficiency, techniques currently in use are attended by significant morbidity and mortality. Most valve repair and replacement procedures require a thoracotomy, to gain access to the patient's thoracic cavity. Surgical intervention within the heart frequently requires isolation of the heart and coronary blood vessels from the remainder of the arterial system and arrest of cardiac function, using a cardiopulmonary bypass machine. Open chest techniques with large sternum openings are used. Those patients undergoing such techniques often have scarring retraction, tears or fusion of valve leaflets, as well as disorders of the subvalvular apparatus.

Naturally, surgical patients desire operations that are performed with the least amount of intrusion into the body. Recently, a great amount of research has been done to reduce the trauma and risk associated with conventional open heart valve replacement surgery. In particular, the fields of minimally invasive surgery (MIS) and percutaneous surgery have exploded since the early to mid-1990s, with devices now being proposed to enable valve repair without opening the chest cavity, and some without even requiring bypass. Proposed MIS heart valve repair procedures are accomplished via elongated tubes or cannulas introduced through one or more small access incisions in the thorax, with the help of endoscopes and other such visualization techniques. For example, see U.S. Pat. No. 6,602,288 to Cosgrove. Such minimally invasive procedures usually provide speedier recovery for the patient with less pain and bodily trauma, thereby reducing the medical costs and the overall disruption to the life of the patient. A minimally invasive approach also usually results in a smaller incision and, therefore, less scarring, which is an aesthetic advantage attractive to most patients.

What is needed are devices and methods for carrying out heart valve repair that reduce the trauma, risks, recovery time and pain that accompany current techniques.

SUMMARY OF THE INVENTION

The present application provides an annuloplasty ring comprising a flexible braided cable extending around the entire periphery of the ring in either a closed or open shape. The annuloplasty rings disclosed herein may have a flexible core member comprises a multi-stranded braided cable. Desirably, the multi-stranded braided cable has at least seven braided cables in cross-section, and may comprise strands of at least two different metals braided together.

In one embodiment a multi-stranded cable replaces solid core wire for both the tricuspid and mitral valves. Cable allows for greater deployment flexibility for minimally-invasive surgical (MIS) implant, while still maintaining the required strength and similar tensile properties of solid-core wire. Cable results in a MIS annuloplasty ring with sufficient flexibility in the x-y plane to allow a surgeon to squeeze the ring into a 1 cm×1 cm incision, while maintaining structural rigidity under forces exerted on the implanted ring by the cardiac cycle and allowing for asymmetrical deflection to be designed into the product. A majority of the length of the inner core member has a first elastic modulus sufficiently flexible to enable the core member to be compressed from its relaxed ring shape into a narrow shape suitable for passage through a tubular access device.

In one embodiment of the invention there is contemplated a method for forming an annuloplasty ring, comprising providing a flexible core member formed from a braided metal cable. The core member is held in a desired peripheral shape of the annuloplasty ring, and then heated above its austenitic final temperature. That temperature is maintained for a period of time, and then the core member is rapidly cooled. A suture-permeable outer covering is added around the flexible core member to form the annuloplasty ring. The metal core member is preferably formed from a multi-stranded braided cable formed of multiple wire strands wound into multi-strand braids with the multi-strand braids being braided into the multi-stranded braided cable. In some embodiments, the multi-stranded braided cable has at least seven multi-strand braids in cross-section and has sufficient flexibility to enable it to be manipulated into an elongated shape to fit within a small tubular access device. The peripheral shape of the core member can be closed or open with two free ends, and if open, the method can include capping or welding the two free ends to cover individual strand ends. The braided metal cable can be made of MP35N LT or Nitinol.

A holding fixture can be provided, the fixture having a base member and at least one clamping member. The base member and clamping member have complementary channels that together provide a three-dimensional mold for the desired peripheral shape of the annuloplasty ring. The step of holding the core member comprises placing the core member between the base member and the at least one clamping member. In some instances, the desired peripheral shape of the annuloplasty ring is open with two free ends. In such case, the holding fixture preferably has three clamping members: a first one for a closed side of the core member and two other for the two free ends. The clamping members are placed sequentially over the core member with the first clamping member first and the two others second and third.

The desired peripheral shape of the annuloplasty ring can be three-dimensional, and the base member and three clamping members have raised areas such that the channel defines the three-dimensional peripheral shape. In some cases, the clamping members bolt to the base member to hold the core member firmly in the channel.

In another embodiment, there is provided an annuloplasty ring comprising a flexible core member comprising a braided metal cable. The cable is formed of a metal that has been heat set by exposure to a temperature above its austenitic final temperature for a period of time to cause a crystalline structure alteration from martensitic to austenitic, and a change in the lowering of the austenite-martensite transition temperature such that the molecules are in the austenitic phase at room temperature. The core member is preferably shaped for mitral or tricuspid implantation, and includes a suture-permeable outer covering around the flexible core member.

In one embodiment, the core member of the annuloplasty ring defines a saddle shape with both a posterior portion and an anterior portion defined by two free ends rising upward from left and right sides. The core member can include a cap or weld on the two free ends to cover individual strand ends.

In some embodiments, the core member is made from a multi-stranded braided cable formed of multiple wire strands wound into multi-strand braids with the multi-strand braids being braided into the multi-stranded braided cable. The multi-stranded braided cable has at least seven multi-strand braids in cross-section, and has sufficient flexibility to enable it to be manipulated into an elongated shape to fit within a small tubular access device. The metal core is preferably made of MP35N LT or Nitinol.

A further understanding of the nature and advantages of the invention will become apparent by reference to the remaining portions of the specification and drawings.

BRIEF DESCRIPTION OF THE DRAWINGS

FIGS. 2A and 2B are plan and elevational views, respectively, of the exemplary annuloplasty ring shown in FIG. 1;

FIGS. 3A-3C are posterior, anterior and side elevational views, respectively, of an exemplary inner core member of the annuloplasty ring of FIG. 1 formed of a heat set braided cable;

FIG. 4 is a sectional view through the exemplary annuloplasty ring taken along line 4-4 of FIG. 2B;

FIG. 5 is a sectional view through the annuloplasty ring inner core member taken along line 5-5 of FIG. 3B;

FIG. 11A is a schematic view of a core member of a closed ring squeezed into an elongated shape and passed through a delivery tube; and FIGS. 12A and 12B are schematic views of a core member of an open ring extended into an elongated shape and passed through a delivery tube.

DESCRIPTION OF THE PREFERRED EMBODIMENTS

The present invention provides a number of different annuloplasty rings or repair segments. It should be understood that the term annuloplasty ring or repair segments refers to any generally elongated structure attachable to the native valve annulus and used in annulus repair, whether straight or curved. For example, an annuloplasty ring is conventionally understood to provide either a complete or substantially complete loop sized to correct a misshapen and or dilated native annulus and which is sutured or otherwise attached to the fibrous annulus from which the valve leaflets extend. In many instances, a partial ring or even a straight repair segment may be used around just a portion of the annulus, such as around the posterior edge.

Figure 1:
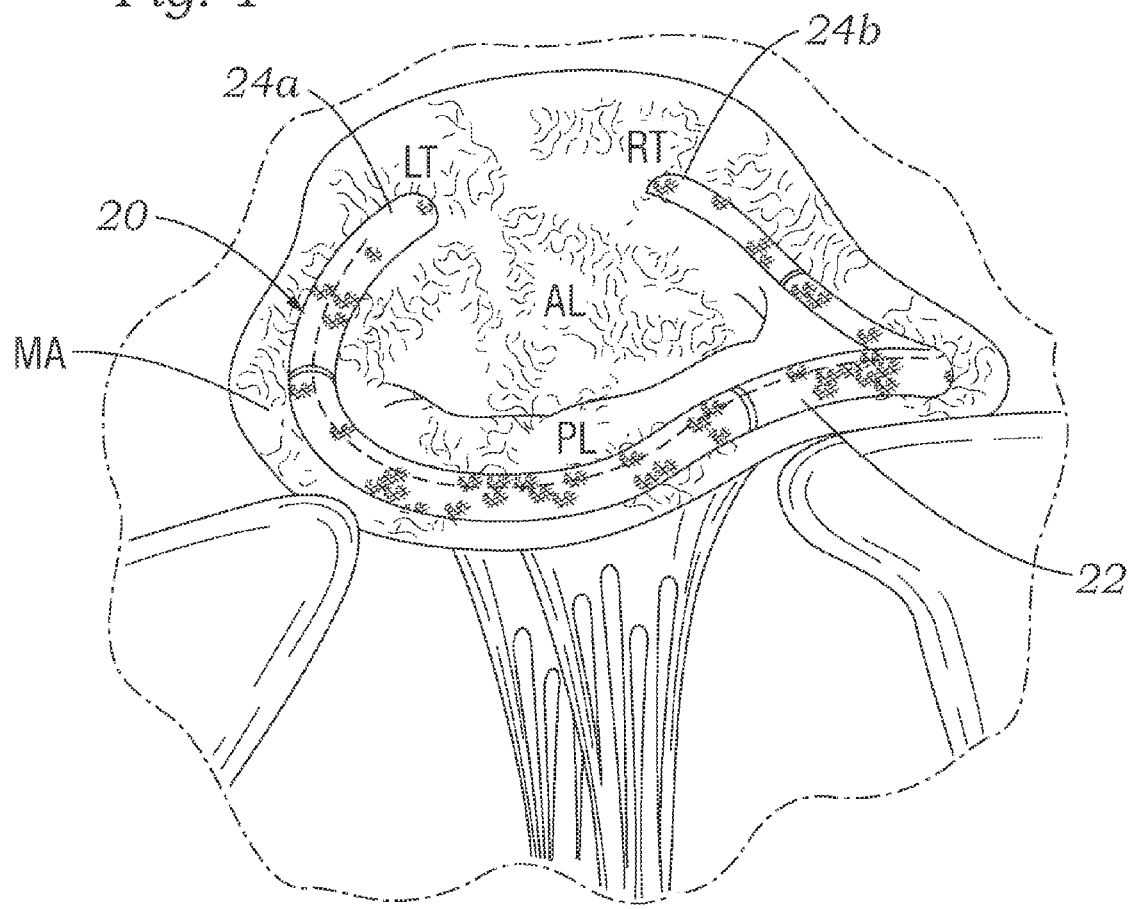
FIG. 1 is a perspective view of an exemplary open annuloplasty ring implanted at a mitral annulus and having free ends that extend significantly past commissure markings.
Figure 2A:
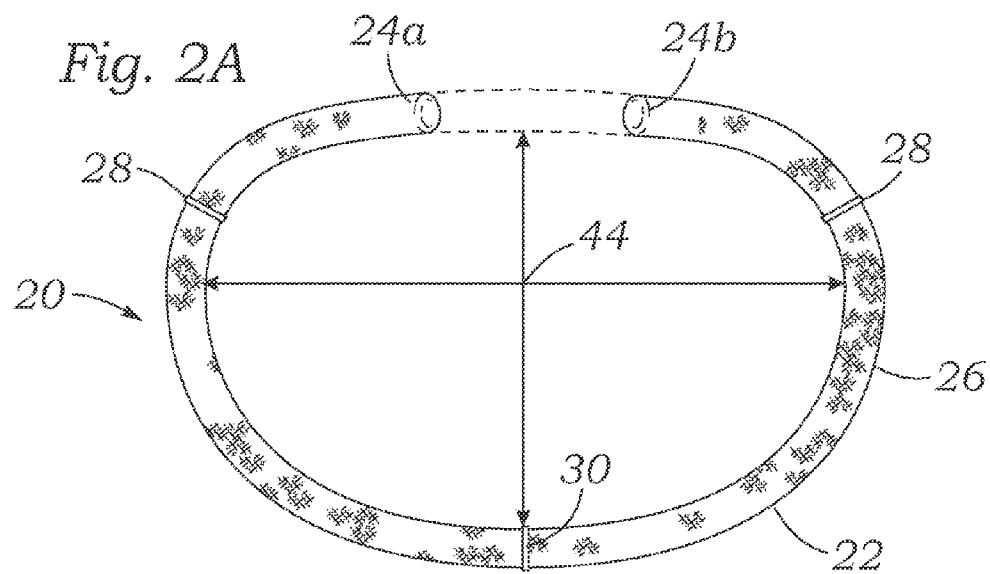

A first embodiment of the present invention is illustrated in FIGS. 1 and 2A-2B in which a mitral annuloplasty ring 20 defines a posterior portion 22 and an anterior portion 24 which has free ends 24a, 24b separated across a gap. Per convention, the annuloplasty ring 20 somewhat resembles an open D-shape with the outwardly convex posterior portion 22 and the free ends 24a, 24b together defining a substantially straight anterior portion extending generally between commissures, or possibly the trigones, of the annulus. The annuloplasty ring 20 typically includes a suture-permeable outer covering 26, described in more detail below, for attaching the ring to the annulus with sutures.

A word about the mitral valve anatomy is necessary. The mitral valve includes a posterior leaflet PL that surrounds approximately two thirds of the circumference of the mitral valve and an anterior leaflet AL that occupies approximately one third of the annular circumference, both of which attach at their outer peripheries at the mitral annulus MA. The conventional representation of these two leaflets shows the posterior leaflet below the anterior leaflet, with their line of coaptation, or contact in the flow stream, as a smile-shaped curve. The mitral valve commissures define distinct areas where the anterior and posterior leaflets come together at their insertion into the annulus—which can be imagined as the corners of the smile-shaped coaptation line. Indeed, the mitral annuloplasty ring 20 includes commissure markings 28 that help the surgeon register or position the ring at the appropriate location around the mitral annulus MA. The markings 28 may be lines of colored thread, whereas the outer covering 26 is typically a white fabric. Ink, toner from a laser printing system or even a yarn knit into the cloth can also be used for marker. A third marking 30 can be provided at the midpoint of the posterior portion 22 of the ring.

The anterior portion of the mitral annulus attaches to the fibrous trigones and is generally more resistant to tearing and less likely to stretch or elongate than the posterior annulus. The right fibrous trigone RT is a dense junctional area between the mitral, tricuspid, non-coronary cusp of the aortic annuli and the membranous septum. The left fibrous trigone LT is situated at the junction of both left fibrous borders of the aortic and the mitral valve. Although the trigones and commissures are proximate to each other, they are not at the exact same location. Indeed, because of the tough, fibrous nature of the trigones, the free ends 24a, 24b of the exemplary annuloplasty ring 20 extend substantially beyond the commissure markings 28, into the area of the trigones RT, LT. In a preferred embodiment, each of the free ends 24a, 24b extends beyond its respective commissure markings 28 (and thus beyond the native commissures) by a length L indicated in FIG. 2B of between about 7-9 mm.

With reference to the posterior elevational view of FIG. 2B, and also the elevational views shown in FIGS. 3A-3C, the three-dimensional contours of the annuloplasty ring 20, and in particular an inner core member 40 will be described. The core member 40 provides a skeleton for the ring 20, and is merely covered with flexible silicone and/or fabric which conforms to its shape. Therefore, the shape of the annuloplasty ring 20 will be described with reference to the shape of the core member 40. The core member 40 has an overall saddle shape, with the posterior portion 22 and anterior portion defined by the free ends 24a, 24b rising upward from left and right sides 42 in between. Although there is a gap between the free ends 24a and 24b, they generally define upward slopes which extend toward one another. The upward rise of the free ends 24a, 24b corresponds to the anterior annulus adjacent to the aortic valve and avoids having a structure that projects into the left ventricular outflow track where it could impede flow out of the aortic valve. This shape also preserves the natural saddle shape of the anterior leaflet of the mitral valve, reducing the stress on the mitral leaflets during systole. Moreover, an imaginary extension can be drawn between the free ends 24a, 24b which is generally smooth and continuous, and defines an upward arc that rises higher than the upward arc of the posterior portion 22, such as shown in dashed lines in FIGS. 2A-2B. The relative height of the anterior portion and the posterior portion 22 of the core member 40 is most evident in the side elevational view of FIG. 3C.

At this point, it is instructive to define coordinate axes for the various directions used to define the ring shape. These definitions are included to aid one of ordinary skill in the art in understanding the geometry of the ring both in and out of the body. The term "axis" or "central axis" 44 in reference to the illustrated ring, and other non-circular or non-planar rings, refers to a line generally perpendicular to the ring that passes through the area centroid of the ring when viewed in plan view (i.e., FIG. 2A). "Axial" or the direction of the "axis" can also be viewed as being parallel to the general direction of blood flow within the valve orifice and thus within the ring when implanted therein; as is known to those of ordinary skill in the art, blood flows normally in a forward direction from the right atrium through the tricuspid valve and into the right ventricle; blood flows normally in a forward direction from the left atrium through the mitral valve and into the left ventricle. Thus, stated another way, the implanted annuloplasty ring orients about a central flow axis aligned along an average direction of normal blood flow through the valve annulus. Although the rings of the present invention are generally 3-dimensional, and saddle-shaped, portions thereof may be planar and lie perpendicular to the flow axis.

Accordingly, with reference to FIGS. 2A-2B and 3A-3C, left and right sides 42 of the core member 40 are located at low points axially, while the midpoint of the posterior portion 22 rises to a high point axially on that side, and the two free ends 24a, 24b rise up to axial high points on the anterior portion. In between the low points and the high points, the core member 40 has gradual curves. The core member 40 when in its relaxed, unstressed state is shaped similar to a Carpentier-Edwards® Physio II™ Annuloplasty Ring available from Edwards Lifesciences of Irvine, Calif. As will be clear below, the open nature of the core member 40, and annuloplasty ring 20 formed thereby, permits a surgeon to open the structure up into an elongated strand for delivery through a small tube such as a catheter or cannula, as will be described below.

FIGS. 3A and 3B illustrate caps or welds 46 formed on the free ends of the core member 40. This is necessary to help prevent fraying of the gradients, and also to minimize abrasion of the surrounding suture-permeable cover at the ends. Depending on the material, laser or plasma welding can be used to melt and form a bead at the ends 46. Alternatively, the ends can be first welded and then a swage die (e.g., Fenn swaging machine) used to round or otherwise even out the weld. Alternatively, a smooth or rounded cap may be welded or adhered to the ends.

FIGS. 4 and 5 shows cross-sections of the ring 20 and exemplary core member 40, respectively. The ring 20 includes the aforementioned core member 40 surrounded by a suture-permeable interface 50, such as a silicone rubber tube. The interface 50 closely surrounds the core member 40, and surrounding that is a fabric cover 52.

As seen in FIG. 5, the illustrated core member 40 desirably comprises a braided cable with multiple cables 54 of braided strands 56 braided amongst themselves. This construction is also known in the art as a multi-stranded braided cable. In the illustrated embodiment, the braid pattern includes 19 separate braided cables 54 of seven strands 56 each, or a 19×7 pattern. Other multi-stranded braids are possible having 7×7, 7×19, 19×7 or even 7×7×7 braided cables. Indeed, even simple cable constructions may be used, such as 1×3, 1×7, or 1×19. Each of these possible braid constructions are seen in FIGS. 10A-10G, and will be described in greater detail below. One example of materials is a cable from Fort Wayne Metals (FWM), 1058 Elgiloy, 19×7 strand arrangement having an overall diameter of 0.062" (1.57 mm). Another is a 7×7 0.069" (0.175 mm) diameter strand arrangement of MP35N LT (again, from FWM) having an overall diameter of 0.062" (1.57 mm).

Figure 6A:
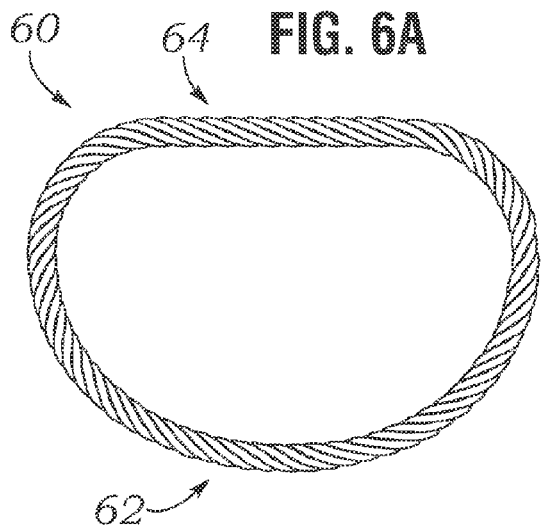
FIGS. 6A and 6B are plan and posterior elevational views, respectively, of an exemplary inner core member having a braided cable for a closed mitral annuloplasty ring.
Figure 6B:
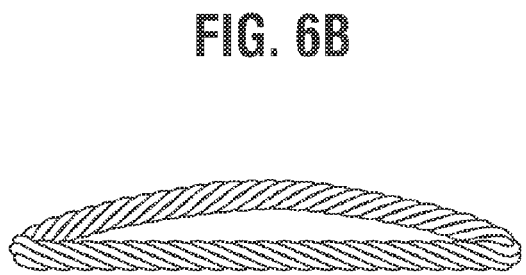

A second embodiment of an annuloplasty ring core member is illustrated in FIGS. 6A and 6B in which the core member 60 for a flexible mitral annuloplasty ring defines a posterior portion 62 and an anterior portion 64. As before, the core member 60 resembles a D-shape with the outwardly convex posterior portion 62 and a substantially straight anterior portion 64. However, in contrast to FIGS. 3A-3C the core member 60 has a closed peripheral shape. An annuloplasty ring that includes the core member 60 may also have a suture-permeable outer covering (not shown), such as a silicone tube surrounding the core member 60 which is then surrounded by a fabric tube, such as seen in FIG. 4. The core member 60 when in its relaxed, unstressed state desirably has the same shape as the Carpentier-Edwards® Physio® Annuloplasty Ring available from Edwards Lifesciences.

Figure 7A:
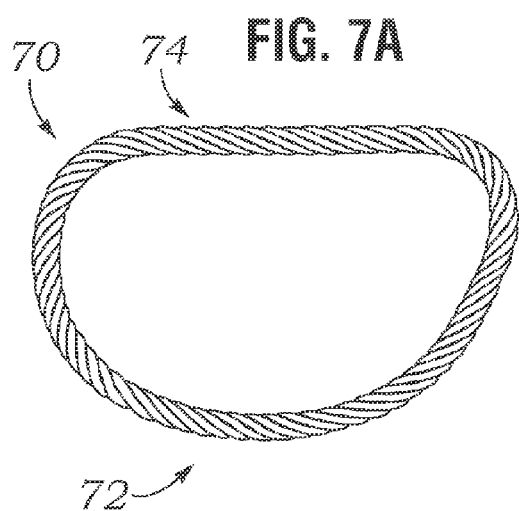
FIGS. 7A and 7B are plan and posterior elevational views, respectively, of an exemplary inner core member having a braided cable for a closed asymmetric mitral annuloplasty ring.
Figure 7B:
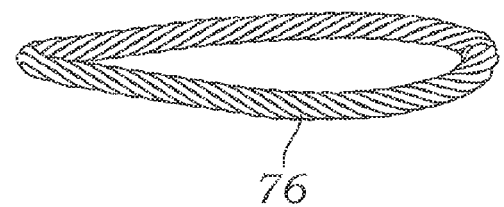

A still further embodiment of the present invention is shown in FIGS. 7A and 7B. A core member 70 for a flexible mitral annuloplasty ring defines a posterior portion 72 and an anterior portion 74. The core member 70 has a modified D-shape with the outwardly convex posterior portion 72 being pulled in on the right side so as to be asymmetric. FIG. 7B shows the right side of the posterior portion dipping downward at 76. As with FIGS. 6A-6B the core member 70 has a closed peripheral shape, but in this embodiment in its unstressed state mimics the shape of the Carpentier-McCarthy-Adams IMR ETlogix™ Annuloplasty Ring, also available from Edwards Lifesciences.

Figure 8A:
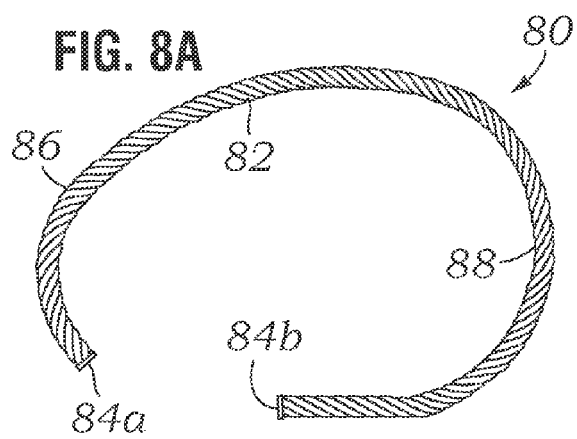
FIGS. 8A and 8B are plan and septal elevational views, respectively, of an exemplary inner core member having a braided cable for an open tricuspid annuloplasty ring.
Figure 8B:
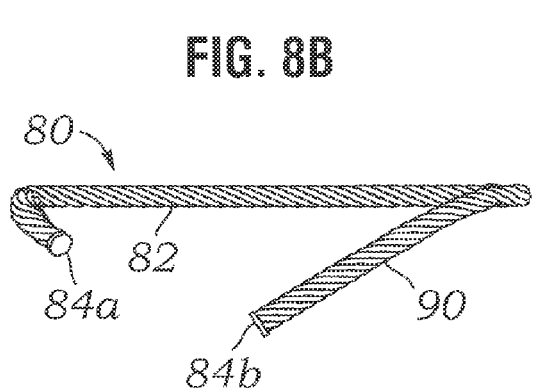

FIGS. 8A and 8B show a still further core member 80 in the shape of a tricuspid annuloplasty ring. As in the earlier embodiments, exterior components such as a silicone interface and fabric cover are not shown to better illustrate the flexible core member 80. The core member 80 includes a flexible braided cable 82 having two free ends 84a, 84b. The core member 80 has the classic tricuspid shape in plan view, starting at the first free end 84a and extending in a clockwise direction around a first segment that ends at a point 86 in the aortic part of the anterior leaflet. Adjacent to the first segment is a second segment corresponding to the remaining part of the anterior leaflet that ends at the postero septal commissure 88. Finally, a third segment 90 extends from the postero septal commissure 88 to the second free end 84b, which is mid-way along the septal leaflet. As seen in FIG. 8B, the third segment 90 angles downward relative to a flow axis (not shown). The nomenclature for these segments is taken from the standard anatomical nomenclature around the tricuspid annulus. The core member 80 when in its relaxed, unstressed configuration is the same shape as an Edwards MC³ Annuloplasty System available from Edwards Lifesciences. Alternatively, although not shown, the unstressed configuration may have the same shape as a Carpentier-Edwards Physio Tricuspid Annuloplasty Ring, such as described in U.S. Patent Publication No. 2012/0071970, filed Aug. 30, 2011, the contents of which are expressly incorporated herein by reference.

The various braided cables that may be used for core members for the annuloplasty rings described herein have a great degree of elasticity and flexibility, and prior to any special processing are unable to form the three-dimensional ring-shapes described above. That is, they tend to spring back to their original braided shape, which is typically linear. Consequently, the present application contemplates heat setting the core members to fix particular desirable shapes therein. Heat setting or more generally heat treatment involves elevating the temperature of the flexible core member while maintaining it in a ring-shaped neutral position using a fixture, which shape remains after quenching and removal from the fixture. More specifically, applied heating can instigate a "heat memory effect," which is essentially when the material is heat treated to retain a specific form, different from its original geometry. After the material has been heated, cooled, and brought back to room temperature, it will naturally remain in the constrained shape. Some terms of the art are presented below, with Nitinol referenced as a potential candidate material:

As (Austenite Start Temperature): Temperature where material begins to transform into austenite. Internal crystalline structure begins to change. For Nitinol, this change normally occurs around 500° C.

Af (Austenite Final Temperature): Temperature where material has completed transforming to austenite.

The aim of the processing is to cause the core member material to remain in its austenitic form after being heated to a particular temperature range, such as from 500° C. to 600° C., for a period of time. The core member will be rigidly constrained in its desired shape and heat treated. The metal is exposed to a temperature above its austenitic final temperature for a period of time to cause its crystalline structure to be altered from martensitic to austenitic, and its austenite-martensite transition temperature is lowered such that the molecules are in the austenitic phase at room temperature. The heat treating essentially "relaxes" the stress initially within the material so that it does not spring back to its unformed shape. Cooling should be rapid to avoid aging effects; for instance a water quench or air cooling may be required. The duration of heating should be sufficient such that the core member reaches the desired temperature throughout its cross-section, which depends on the mass of the holding fixture, the material, as well the heating method.

Various studies have been done with metals that are good candidates for use in cardiac implants. Table I, below, indicates performance parameters for two NiTi cable samples which were heated in a ring fixture at temperatures ranging from 500° C.-600° C. The resulting shape retention and other relevant notes were recorded for the stress relieved (STR), and the non-stress relieved (Non STR) NiTi samples in Table I. The NiTi tested was comprised of approximately 56% Nickel and 44% Titanium. The ring samples were stretched from their new neutral positions after heat treatment and released to see if they returned to its constrained shape during heat treating. These tests revealed that a treatment temperature of 550° C. for either material resulted in good shape retention.

TABLE I

Results of Heat Treating Nitinol (NiTi)

| | Temperature | | |
|---|---|---|---|
| | 500° C. | 550° C. | 600° C. |
| STR | Did not fully return to original jig (constrained) position No cracking | Fully returned to original jig position. More spring back force than at 500° C. Minimal cracking | Fully returned to original jig position. More spring back force than at 550° C. More cracking than 550° |
| Non STR | Did not fully return to original jig (constrained) position No cracking | Fully returned to original jig position. More springback force than at 500° C. Minimal cracking | Fully returned to original jig position. More spring back force than at 550° C. More cracking than 550° |

In addition to the characterization of the NiTi samples, heat shaping characterization was also conducted using samples of a new alloy developed by Fort Wayne Metals (FWM) denoted MP35N LT. MP35N LT is a composition which is mainly Nickel, Chromium and Molybdenum. The samples were treated at 500° C., 600° C., and 700° C. The 700° C. showed the greatest shape retention and proved MP35N LT can be heat shaped as well.

From these tests both NiTi and MP35N LT cables showed promise. However, while highly resistant to permanent deformation, NiTi cables are likely to lose their passivation layer during heat shaping, which makes it a less ideal cable choice than the MP35N LT cable type. One possibility is to form the core member from strands of at least two different metals braided together for a particular performance outcome. NiTi is a highly flexible material that may not require the braided construction to get a 3-D shape that can be flexed to go through a 1 cm catheter. On the other hand, for CoCr alloys (e.g., MP35N LT) the braided structure is necessary. Nevertheless, MP35N LT has superior fatigue resistance compared to NiTi, which is a significant factor in a system that must flex 40K times per year for most of a patient's remaining lifetime (average of 10-20 years). Consequently, CoCr alloys are preferred, with MP35N LT being especially desirable.

In a preferred embodiment of an annuloplasty ring, a core member 40 such as shown in FIGS. 3A-3C was heat set to have the following characteristics:

The percent ratio of the minor axis to the major axis is 75%±10%. The percent ratio of the height of the posterior portion 22 relative to the major axis dimension is 5±2%. The distance apart on the free ends 24a, 24b, or the gap there between, relative to the major axis dimension is 52±5%. The material used is MP MP35N LT 7×7 stranded cable available from Fort Wayne Metals. Finally, the proportional shapes of the rings change over a set of rings having nominal sizes of 24-44 mm. First of all, the percent ratio of the height of the free ends 24a, 24b relative to the major axis dimension is 5±3% for ring sizes of 24-28 mm, and 15±3% for larger ring sizes of 30-44 mm. Also, the plan view shape changes over the set of rings, with the ratio of the minor axis to the major axis preferably increasing for ring sizes 30 mm and above to go from generally D-shaped to becoming more circular.

The exemplary process for heat setting the core member 40 is to place it in a fixture in a vacuum furnace at 775° centigrade for 20 minutes. Argon then flooded the chamber for a minimum of one minute. The core member was left in the holding fixture and quenched with water, then removed and allowed to dry. At this point, the free ends of the core member 40 are welded and/or capped, and the entire core member is electropolished. A suitable cleaning process is then done to ensure removal of any metal particles from the fabrication. Subsequently, the suture-permeable cover is added, as indicated in FIG. 4.

Figure 9A:
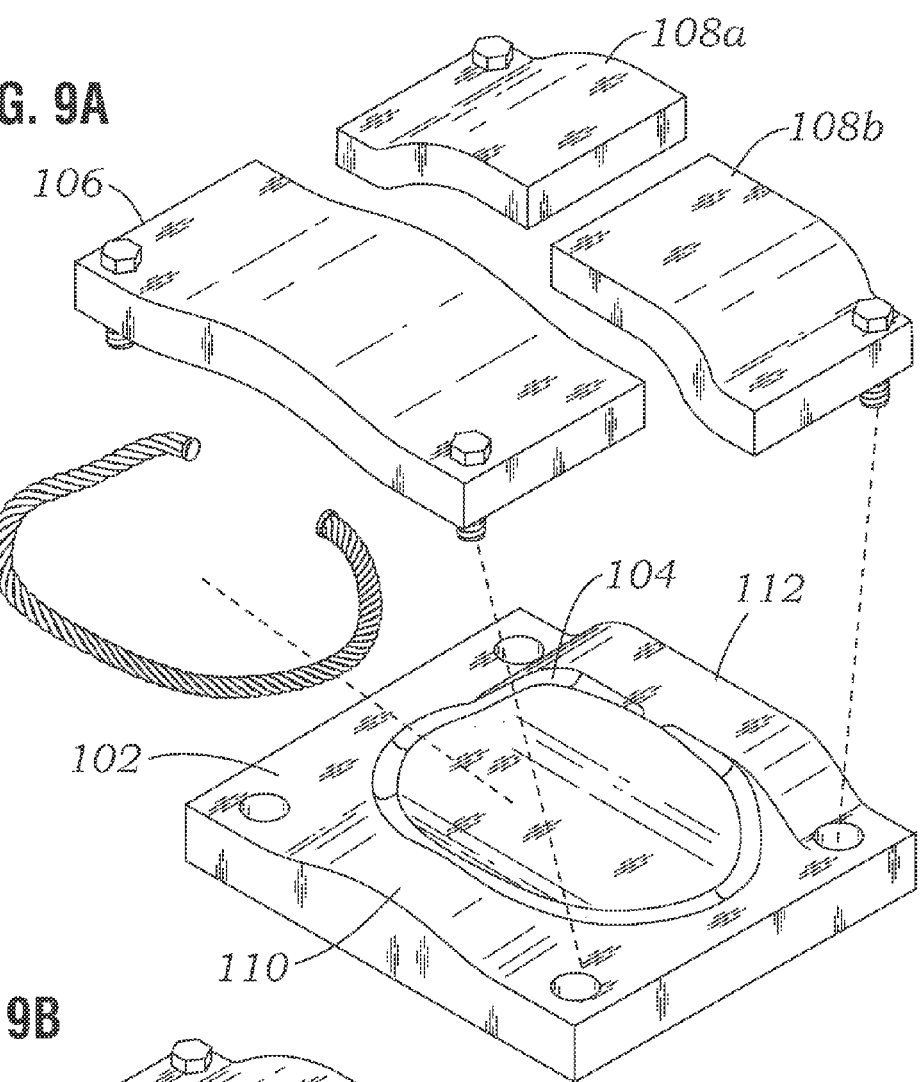
FIG. 9A is a perspective view of the core member from FIGS. 3A-3C seen exploded with an exemplary fixture for holding the core in a desired shape during a heat setting procedure.
Figure 9B:
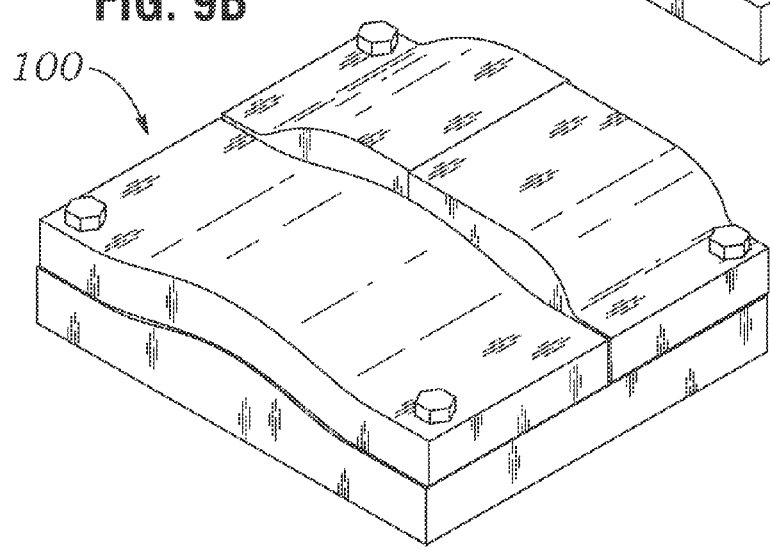
FIG. 9B is a perspective view of the assembled fixture for holding the core in a desired shape during a heat setting procedure.
Figure 10A:
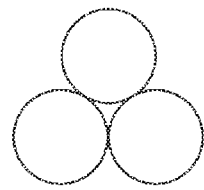
FIGS. 10A-10G show a number of different possible braided cable configurations that may be used.
Figure 10B:
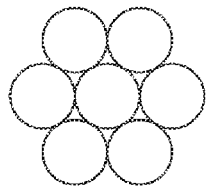
Figure 10C:
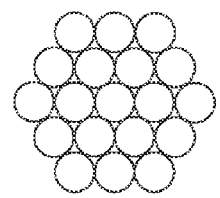
Figure 10D:
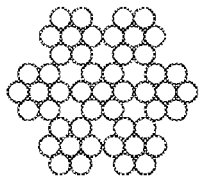
Figure 10E:
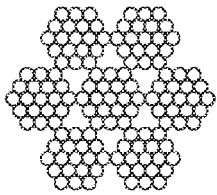
Figure 10F:
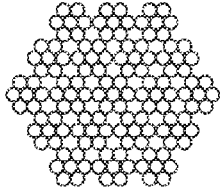
Figure 10G:
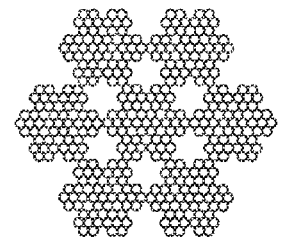

FIGS. 9A and 9B illustrate exploded and assembled views of an exemplary holding fixture 100 for the core member 40. The fixture comprises a base member 102 having a generally rectangular periphery and defined therein a channel 104 shape to hold the core member 40. Of course, a core member 40 initially starts out as a straight or slightly curved cable, and is positioned within the channel 104 beginning on a front side (toward the reader). Above the base member 102, three clamp members 106 and 108a, 108b are shown. The clamp members 106, 108 fasten to the base member 102 using bolts 110, or the like. After the proximal side of the core member 40 is seated within the channel 104, the larger of the clamp members 106 is placed thereover and secured to the base member 102. The clamp member 106 covers approximately half of the area of the base member 102. At this point, the free ends of the core member 40 project out from between the base member 102 and the front clamp member 106. The smaller clamp members 108a, 108b are symmetric and shaped to each hold down one of the free ends of the core member 40. Each free end is thus pushed down one at a time into the corresponding portion of the channel 104 and one of the clamp members 108a, 108b is secured to the base member 102. In this way, the process for loading the core member 40 into the holding fixture 100 is easily accomplished in sections.

It should be noted that the base member 102 has a three-dimensional contour that provides a mold for the final shape of the core member 40. For example, a front end 110 of the base member 102 shows a slight upward bow such that the same curve can be imparted to the posterior portion of the core member 40. Likewise, a rear end 112 features a raised contour that imparts the upward curvatures to the free ends of the core member 40. The precise mold shape for the core member 40 is defined by the channel 104 which generally follows the contours of the base member 102. Although not shown, an opposite half of the channel is provided in the underside of the clamp members 106, 108 such that the core member 40 is surrounded by a generally cylindrical channel around its entire periphery. This prevents any movement and imparts a precise shape to the core member 40 in the heat setting process. The heat setting of the core members thus fixes defined bends where desired in the final shape.

FIGS. 10A-10G show a number of different braided wire configurations that may be used. These include: a simple 1×3 cable in FIG. 10A, a simple 1×7 cable in FIG. 10B, and a simple 1×19 cable in FIG. 10C. Multi-stranded cables include multiple braided cables braided with one another, and include: a 7×7 cable in FIG. 10D, a 7×19 cable in FIG. 10E, a 19×7 cable in FIG. 10F, and a 7×7×7 cable in FIG. 10G. Each of these cables comprises many individual strands that are twisted around each other whereas solid-core wire is composed of a single strand. Even though wide ranges of materials and alloys can be used for both, cable is much more versatile than solid-core wire since different alloys can be used for different strands, different strand counts and geometric placements can be used, and different amounts of coiling can be used. This contrasts the basic nature of solid-core wire where only a single alloy can be used. Because of this unique geometry, cables typically provide a better balance of strength and flexibility. When pulled in tension from both ends, cable acts similarly to wire since the different strands are all being pulled in the same direction. However, when a cable is bent, the stress on the outermost surface of each strand in the cable is proportional to the diameter of the strand. Since each strand in a cable is much smaller than a solid core wire with the same total diameter, the bending stress and resistance to bending force is greatly reduced. This difference provides the increased flexibility as well as improved fatigue properties for a multi-strand cable compared to a solid core wire of the same total diameter. It is this unique property of cable that makes it an attractive alternative to solid-core wire with respect to annuloplasty rings for minimally invasive surgery. More information on medical grade cables is available from Fort Wayne Metals headquartered in Fort Wayne, Ind. In particular, some cables may be coated with inert polymers for greater biocompatibility.

It should be understood that the stranded cable core members described herein are sufficiently elastic so as to be elongated and stressed from their relaxed shapes as shown into a more linear configuration for delivery through an access tube. The rings described herein thus have a relaxed or unstressed shape and a stressed delivery shape. The unstressed shape as shown in the drawings generally describes the shape after implant, though external forces from the surrounding annulus may deflect the unstressed shape a little. Desirably there is a balance between permitting the ring to elongate for delivery while at the same time being able to remodel to a certain extent the particular annulus consistent with the relaxed shape. Conventional remodeling rings include a more rigid core, such as solid titanium, while wholly flexible rings are typically formed of silicone/cloth combinations or just PET or PTFE cloth, neither of which would be suitable for the present purpose. The solid core rings cannot be deformed to go through a very small incision (e.g. 1 cm), while the entirely flexible rings cannot impart a shape that corrects the anatomy in a pathological valve that is often flattened by the disease process. Consequently, the present rings restore the three dimensional normal anatomical shape to the annulus which can reduce the stress seen in the native leaflets.

FIG. 11A schematically illustrates a core member of a closed annuloplasty ring 114 of the present application squeezed into an elongated shape to fit within a tubular access device 116. The flexible cable 118 facilitates the conversion from D-shaped to linear so that the ring 114 may be introduced to an implant site through the access device 116. The access device 114 may be a cannula or introducer tube, or other similar expedient.

FIGS. 12A and 12B schematically illustrate a technique for delivering an annuloplasty ring having a core member 120 in a minimally-invasive manner. Because of the open nature of the core member 120, with the two free ends, the ring may be opened up or stretched out relatively straight in a stressed state as seen in FIG. 12A and inserted within a tubular access device 122. The access device 122 may be inserted through an access port in the patient's chest, for example, so that its distal end is positioned at the tricuspid annulus. The core member 120 is seen being expelled from one end of the access device 122 in FIG. 12B and immediately starts assuming its relaxed unstressed state. In practice, the ring will be expelled from the distal end of the access device 122 so as to assume the unstressed ring shape in approximately the proper implant location, at which time sutures or staples may be used to attach the ring to the annulus.

These delivery methods are enabled by the multi-stranded cables described herein which have the flexibility to accommodate large amounts of bending without permanent deformation. Desirably, the stranded cable rings described herein may be passed through less-invasive access catheters or the like having a size of 18 Fr, 16 Fr, 14 Fr or even smaller. However, the disadvantage of cable is that it is not as easy to permanently shape into a ring. This issue is addressed by heat setting the core members to fix defined bends where desired.

Although the present application contemplates using both simple (i.e., single braided) and multi-stranded (i.e., multiple braids intertwined) cables, multi-stranded cables are believed better suited for the MIS delivery approach. For open rings, simple cables may be easily stretched linearly for passage through an access tube, but once permitted to relax and resume the annuloplasty ring shape, these simple cables may not have the requisite stiffness for annulus remodeling. As such, a greater number of bends would have to be used, which may place undesirable limitations on overall ring performance. Furthermore, simple cables formed into closed rings may not be able to be squeezed into a linear shape without kinking into permanent bends. On the other hand, multi-stranded cables are more flexible in bending due to their generally smaller individual strands and the ability of those strands to slide with respect to one another. Moreover, in open rings multi-stranded cables retain larger stiffness in the plane of the ring to provide good remodeling. This is not to say that simple cables are excluded from the present application, an annuloplasty ring that is not delivered through a small access port may be made of simple cable that is heat set to a particular shape and performs suitably.

Preliminary Evaluation of Fort Wayne Metals Cable Samples

A. Semi-Quantitative Analysis of Cable Samples

A series of cable samples, representing typical standard products for biomedical applications, was provided by Fort Wayne Metals (FWM). Table II summarizes physical properties of the samples. It should be noted that these are not the only materials contemplated, and the list of suitable materials includes alloys of stainless steel, Titanium, Titanium Alloys, Cobalt Chromium, Nitinol (NiTi) and Nickel Alloys. Further, blends or combinations of these various materials could be utilized to obtain particular performance characteristics. The number of permutations is essentially limitless.

TABLE II

Cable samples provided by FWM

| Sample | Material | Diameter (in) | Strand Count |
|---|---|---|---|
| 1 | Ti 6Al 4V ELI | 0.0375 | 19 × 7 |
| 2 | Ti 6Al 4V ELI | 0.0423 | 7 × 7 |
| 3 | L-605 | 0.0625 | 19 × 7 |
| 4 | L-605 | 0.080 | 7 × 7 |
| 5 | FWM-1058 | 0.062 | 7 × 19 |
| 6 | 316 LVM | 0.078 | 7 × 7 |
| 7 | 316 LVM | 0.0475 | 1 × 19 |
| 8 | 316 LVM | 0.0425 | 1 × 7 |
| 9 | MP35N | 0.063 | 7 × 7 |
| 10 | FWM-1058 | 0.125 | 7 × 19 |

A preliminary, semi-quantitative analysis was performed on these samples to determine issues with cable material, diameter, and strand count. A minimum bending diameter was determined visually, by bending the cable sample back upon itself until either permanent deformation occurred or cable strands began to separate. At this orientation, measurements were taken by a caliper. The force required to hold this minimum bending diameter was estimated by manually applying the necessary load while the cable was resting on a laboratory scale. Additionally, the cable samples were evaluated for minimum bending diameter with moderate deformation (defined as a ~10 degree bend remaining in the cable after removing load), as well as "robustness", which was based on qualitative observation of how much bending/deformation cables could withstand without suffering permanent damage (kinking, strand separation, or permanent deformation). The results of this preliminary analysis are presented in Table 3.

TABLE III

Results of semi-quantitative analysis on cable samples provided by FWM.

| Sample | Min Dia (mm) | Force (g) | Robustness | Def. Dia (mm) |
|---|---|---|---|---|
| 1 | 6.9 | 48 | F | 4.8 |
| 2 | 9.5 | 130 | G | 6.5 |
| 3 | 14.9 | 228 | G | 9.4 |
| 4 | 25.4 | 460 | G | 13.7 |
| 5 | 12.1 | 185 | G | 8 |
| 6 | 20.4 | 560 | G | 12 |
| 7 | 16.2 | 480 | F | 10.7 |
| 8 | 22.8 | 580 | P | 20 |
| 9 | 17.6 | 385 | G | 9.9 |
| 10 | 16.5 | 410 | G | 10.5 |

Results in Table III may be sorted to identify good (G), acceptable or fair (F), and poor (P) values with respect to the features necessary for use in MIS Annuloplasty Rings. As discussed previously, the ideal characteristic is for a cable to be sufficiently flexible to compress for delivery through a catheter, yet maintain rigidity in the deployed state. Given this, samples that had a minimum bending diameter of <10 mm were considered good, while those with a minimum bending diameter of >20 mm were considered poor. While force to maintain this bending diameter is not a direct measure of cable bending modulus, it is a reasonable indirect measure; for this reason, an arbitrary value of >400 g was considered good, while <200 g was considered poor. One noticeable result was that low-strand-count cables (#7 & #8), were considerably less robust compared to the higher strand count cables.

Among these cable samples, samples 2, 3, 9, & 10 had the best overall relative combination of stiffness, compressibility, and robustness. While it is premature to form specific cable selection recommendations, qualitative observations and this data suggest that a cable diameter of less than 0.08 in, combined with a strand count of 7×7, 7×19, or 19×7, is best suited for annuloplasty ring applications.

B. Cable Selection Considerations

Preliminary evaluation of FWM samples are consistent with the results of computer simulations, with both indicating that a wide variety of cable materials could be used for annuloplasty ring applications. Since the eventual core shape will dictate the effective modulus of a given cable type, material selection is not constrained by the inherent stiffness of the cable material. A likely cable selection strategy is to:

Select material based on availability/familiarity.

Select cable diameter to be similar in diameter to current "solid-core" rings.

Select a standard, off-the-shelf cable, with moderate strand count and low bending modulus, to achieve maximum compression for delivery through catheter.

Iterate with greater strand count if local maximum displacements are too great.

Thus a flexible cable provides the ring with sufficient flexibility to compress for delivery through a catheter, while maintaining rigidity in the deployed state. Prototypes have been constructed employing this strategy. It is also possible to combine multiple cable types to achieve the combination of high bending for deployment as well as high post-deployed stiffness.

While the foregoing is a complete description of the preferred embodiments of the invention, various alternatives, modifications, and equivalents may be used. Moreover, it will be obvious that certain other modifications may be practiced within the scope of the appended claims.

What is claimed is:

1. A method for forming an annuloplasty ring, comprising:

providing a flexible core member comprising a braided metal cable made of a metal having an austenite start temperature of at least 500° C.;

providing a holding fixture having a base member and at least one clamping member, wherein the base member and clamping member have complementary channels therein that together provide a three-dimensional mold for the desired peripheral shape of the annuloplasty ring;

holding the core member in a desired peripheral shape of the annuloplasty ring by placing the core member between the base member and the at least one clamping member;

while being held in the desired peripheral shape, heating the core member above its austenitic final temperature and maintaining that temperature for a period of time to cause a crystalline structure alteration from martensitic to austenitic;

cooling the core member with a quench; and adding a suture-permeable outer covering around the flexible core member.

2. The method of claim 1, wherein the core member comprises a multi-stranded braided cable formed of multiple wire strands wound into multi-strand braids with the multi-strand braids being braided into the multi-stranded braided cable.

3. The method of claim 2, wherein the multi-stranded braided cable has at least seven multi-strand braids in cross-section.

4. The method of claim 1, wherein the braided cable has sufficient flexibility to enable it to be manipulated into an elongated shape to fit within a tubular access device.

5. The method of claim 1, wherein the peripheral shape is closed.

6. The method of claim 1, wherein the peripheral shape is open with two free ends.

7. The method of claim 6, wherein the method includes capping or welding the two free ends to cover individual strand ends.

8. The method of claim 1, wherein the metal is MP35N LT.

9. The method of claim 1, wherein the metal is Nitinol.

10. The method of claim 1, further comprising providing a holding fixture having a base member and at least one clamping member, wherein the base member and clamping member have complementary channels therein that together provide a three-dimensional mold for the desired peripheral shape of the annuloplasty ring, and wherein the step of holding the core member comprises placing the core member between the base member and the at least one clamping member.

11. The method of claim 10, wherein the desired peripheral shape is open with two free ends, and the holding fixture has three clamping members: a first one for a closed side of the core member and two others for the two free ends, and wherein the method includes placing the clamping members sequentially over the core member with the first clamping member first and the two others second and third.

12. The method of claim 11, wherein the desired peripheral shape is three-dimensional, and the base member and three clamping members have raised areas such that the channel defines the three-dimensional peripheral shape.

13. The method of claim 11, wherein clamping members bolt to the base member to hold the core member firmly in the channel.

* * * * *